United States Patent
Leduc et al.

(10) Patent No.: US 11,478,386 B2
(45) Date of Patent: Oct. 25, 2022

(54) ABSORBENT PRODUCTS FOR ARTICLES OF CLOTHING

(71) Applicant: BOUTIQUE LA VIE EN ROSE INC., Montréal (CA)

(72) Inventors: Steve Leduc, Saint-Andre-Avellin (CA); Fanny-Maude Theberge, Saint-Andre-Avellin (CA)

(73) Assignee: BOUTIQUE LA VIE EN ROSE INC., Montreal (CA)

( * ) Notice: Subject to any disclaimer, the term of this patent is extended or adjusted under 35 U.S.C. 154(b) by 719 days.

(21) Appl. No.: 16/329,422

(22) PCT Filed: Aug. 28, 2017

(86) PCT No.: PCT/CA2017/051006
§ 371 (c)(1),
(2) Date: Feb. 28, 2019

(87) PCT Pub. No.: WO2018/039780
PCT Pub. Date: Mar. 8, 2018

(65) Prior Publication Data
US 2019/0247243 A1    Aug. 15, 2019

Related U.S. Application Data

(60) Provisional application No. 62/494,939, filed on Aug. 29, 2016, provisional application No. 62/477,654, filed on Mar. 28, 2017.

(51) Int. Cl.
*A61F 13/505* (2006.01)
*A61F 13/47* (2006.01)
(Continued)

(52) U.S. Cl.
CPC ............ *A61F 13/505* (2013.01); *A61F 13/15* (2013.01); *A61F 13/47* (2013.01); *A61F 13/475* (2013.01);
(Continued)

(58) Field of Classification Search
CPC .............. A61F 13/15268; A61F 13/505; A61F 13/534; A61F 13/56; A61F 13/5605;
(Continued)

(56) References Cited

U.S. PATENT DOCUMENTS 3,608,551 A * 9/1971 Seijo ....................... A61F 13/74
604/396
4,352,356 A * 10/1982 Tong ..................... A61F 5/4401
604/372

(Continued)

FOREIGN PATENT DOCUMENTS

CN    2151784 Y    1/1994
CN    2169440 Y    6/1994
(Continued)

OTHER PUBLICATIONS

English Abstract of FR2903865; Retrieved on May 25, 2019; Retrieved from www.worldwide.espacenet.com.
(Continued)

*Primary Examiner* — Catharine L Anderson
(74) *Attorney, Agent, or Firm* — Benoit & Cote, Inc.; Mathieu Miron

(57) ABSTRACT

The present technology relates to an absorbent product for attachment to an article of clothing. The absorbent product comprises a wearer-facing surface and a garment-facing surface opposite the wearer-facing surface. The absorbent product comprises a main body, wherein the main body comprises: a central absorbent core; an external envelope placed around the central core and having a front extremity
(Continued)

and a rear extremity; a first attachment line located at the front extremity of the external envelope; and a second attachment line located at the rear extremity of the external envelope; wherein the first attachment line and the second attachment line are for attachment of the absorbent product to the article of clothing; and wherein the absorbent product is free of means for adhesively attaching the garment-facing surface to the article of clothing.

20 Claims, 7 Drawing Sheets

(51) Int. Cl.
<table>
<tr><td>A61F 13/72</td><td>(2006.01)</td></tr>
<tr><td>A61F 13/475</td><td>(2006.01)</td></tr>
<tr><td>A61F 13/56</td><td>(2006.01)</td></tr>
<tr><td>A61F 13/15</td><td>(2006.01)</td></tr>
<tr><td>A61F 13/66</td><td>(2006.01)</td></tr>
</table>

(52) U.S. Cl.
CPC .......... *A61F 13/56* (2013.01); *A61F 13/5605* (2013.01); *A61F 13/665* (2013.01); *A61F 13/72* (2013.01)

(58) Field of Classification Search
CPC ............... A61F 13/665; A61F 13/72; A61F 2013/15276; A61F 2013/53445; A61F 2013/5694
See application file for complete search history.

(56) References Cited

U.S. PATENT DOCUMENTS

| | | | | |
|---|---|---|---|---|
| 4,695,279 | A * | 9/1987 | Steer | A61F 5/4401 2/406 |
| 5,669,902 | A * | 9/1997 | Sivilich | A61F 5/4401 604/385.14 |
| 6,530,091 | B2 * | 3/2003 | Takai | A61F 13/505 2/406 |
| 6,807,685 | B1 * | 10/2004 | Hasegawa | A61F 13/74 2/406 |
| 8,690,695 | B1 | 4/2014 | Pillman | |
| 2002/0169432 | A1 * | 11/2002 | Fell | A61F 13/505 604/385.14 |
| 2003/0002528 | A1 * | 1/2003 | Krieps | A61F 13/496 370/468 |
| 2008/0183148 | A1 | 7/2008 | Labit et al. | |
| 2011/0172621 | A1 * | 7/2011 | Lee | A61F 13/505 604/365 |
| 2013/0019373 | A1 | 1/2013 | Strong | |
| 2016/0106556 | A1 | 4/2016 | Van der Watt et al. | |

FOREIGN PATENT DOCUMENTS

| | | |
|---|---|---|
| CN | 2213449 Y | 11/1995 |
| CN | 2396657 Y | 9/2000 |
| CN | 2650753 Y | 10/2004 |
| CN | 2787017 Y | 6/2006 |
| CN | 2805836 Y | 8/2006 |
| CN | 200990862 Y | 12/2007 |
| CN | 201076016 Y | 6/2008 |
| CN | 201101874 Y | 8/2008 |
| CN | 201127831 Y | 10/2008 |
| CN | 201319913 Y | 10/2009 |
| CN | 201336945 Y | 11/2009 |
| CN | 201337629 Y | 11/2009 |
| CN | 201353231 Y | 12/2009 |
| CN | 101485563 B | 6/2011 |
| CN | 203416820 U | 2/2014 |
| CN | 203467687 U | 3/2014 |
| CN | 203597420 U | 5/2014 |
| CN | 104095306 A | 10/2014 |
| CN | 204335959 U | 5/2015 |
| CN | 204492105 U | 7/2015 |
| CN | 204769762 U | 11/2015 |
| EP | 1869996 B1 | 12/2008 |
| FR | 2903865 A1 | 1/2008 |
| FR | 2931628 A1 | 12/2009 |
| FR | 2983081 A | 5/2013 |
| JP | 10314362 A | 12/1998 |
| KR | 100773060 B1 | 11/2007 |
| KR | 20090116324 A | 11/2009 |
| KR | 20130117123 A | 10/2013 |
| WO | WO9409661 A1 | 5/1994 |
| WO | WO2015024969 A1 | 2/2015 |
| WO | 2016053724 A1 | 4/2016 |

OTHER PUBLICATIONS

English Abstract of EP1869996; Retrieved on Jun. 3, 2019; Retrieved from www.worldwide.espacenet.com.
English Abstract of KR100773060; Retrieved on Jun. 3, 2019; Retrieved from www.worldwide.espacenet.com.
English Abstract of CN204769762; Retrieved on Jun. 3, 2019; Retrieved from www.worldwide.espacenet.com.
English Abstract of CN204492105; Retrieved on Jun. 3, 2019; Retrieved from www.worldwide.espacenet.com.
English Abstract of CN204335959; Retrieved on Jun. 3, 2019; Retrieved from www.worldwide.espacenet.com.
English Abstract of CN104095306; Retrieved on Jun. 3, 2019; Retrieved from www.worldwide.espacenet.com.
English Abstract of CN203597420; Retrieved on Jun. 3, 2019; Retrieved from www.worldwide.espacenet.com.
English Abstract of CN203467687; Retrieved on Jun. 3, 2019; Retrieved from www.worldwide.espacenet.com.
English Abstract of CN203416820; Retrieved on Jun. 3, 2019; Retrieved from www.worldwide.espacenet.com.
English Abstract of CN201353231; Retrieved on May 25, 2019; Retrieved from www.worldwide.espacenet.com.
English Abstract of CN201337629; Retrieved on May 25, 2019; Retrieved from www.worldwide.espacenet.com.
English Abstract of CN201336945; Retrieved on May 25, 2019; Retrieved from www.worldwide.espacenet.com.
English Abstract of CN201319913; Retrieved on May 25, 2019; Retrieved from www.worldwide.espacenet.com.
English Abstract of CN101485563; Retrieved on May 25, 2019; Retrieved from www.worldwide.espacenet.com.
English Abstract of CN201127831; Retrieved on May 25, 2019; Retrieved from www.worldwide.espacenet.com.
English Abstract of CN201101874; Retrieved on May 25, 2019; Retrieved from www.worldwide.espacenet.com.
English Abstract of CN201076016; Retrieved on May 25, 2019; Retrieved from www.worldwide.espacenet.com.
English Abstract of CN200990862; Retrieved on May 25, 2019; Retrieved from www.worldwide.espacenet.com.
English Abstract of CN2787017; Retrieved on May 25, 2019; Retrieved from www.worldwide.espacenet.com.
English Abstract of CN2805836; Retrieved on May 25, 2019; Retrieved from www.worldwide.espacenet.com.
English Abstract of CN2396657; Retrieved on May 25, 2019; Retrieved from www.worldwide.espacenet.com.
English Abstract of CN2213449; Retrieved on May 25, 2019; Retrieved from www.worldwide.espacenet.com.
English Abstract of CN2169440; Retrieved on May 25, 2019; Retrieved from www.worldwide.espacenet.com.
English Abstract of CN2151784; Retrieved on May 25, 2019; Retrieved from www.worldwide.espacenet.com.
English Abstract of CN2650753; Retrieved on May 25, 2019; Retrieved from www.worldwide.espacenet.com.
English Abstract of KR20130117123; Retrieved on May 25, 2019; Retrieved from www.worldwide.espacenet.com.
English Abstract of KR20090116324; Retrieved on May 25, 2019; Retrieved from www.worldwide.espacenet.com.
English Abstract of FR2983081; Retrieved on May 25, 2019; Retrieved from www.worldwide.espacenet.com.

(56) References Cited

OTHER PUBLICATIONS

English Abstract of FR2931628; Retrieved on May 25, 2019; Retrieved from www.worldwide.espacenet.com.
English Abstract of JPH10314362; Retrieved on May 25, 2019; Retrieved from www.worldwide.espacenet.com.
International Search Report and Written Opinion issued in International Application PCT/CA2017/051006 dated Nov. 8, 2017.

* cited by examiner

ABSORBENT PRODUCTS FOR ARTICLES OF CLOTHING

CROSS-REFERENCE TO RELATED APPLICATIONS

This application claims the benefit of and priority to U.S. provisional patent application No. 62/494,939, filed Aug. 29, 2016 and the benefit of and priority to U.S. provisional patent application No. 62/477,664, filed on Mar. 28, 2017; the content of both of these U.S. provisional patent applications is herein incorporated in entirety by reference.

FIELD OF TECHNOLOGY

The present technology generally relates to absorbent products for placement into articles of clothing. In particular, the present technology relates to a washable and reusable absorbent product for placement into undergarments such as underpants. The present technology also generally relates to washable and reusable articles of clothing (e.g., undergarments) having such absorbent product.

BACKGROUND INFORMATION

Many women experience urinary leakage or loss of body fluids. Non-reusable underpants and reusable undergarments which fit the wearer's undergarment are currently being used by these women to alleviate the discomfort they are experiencing. However, the currently proposed undergarments are designed with assembly seams located edges (or extremities) of the absorbent core. The perforations caused by the seams channel body fluids and cause liberation (leaks) of body fluids accumulated in the absorbent core.

There is thus a need in this field of technology for absorbent products that prevent leakage of the body fluids and prevent the wearer from being wetted during movements or activities and for articles of clothing comprising such absorbent products.

SUMMARY OF DISCLOSURE

According to various aspects, the present disclosure provides an absorbent product for attachment to an article of clothing, the absorbent product comprising a wearer-facing surface and a garment-facing surface opposite the wearer-facing surface, the absorbent product comprising a main body, wherein the main body comprises a central absorbent core; an external envelope placed around the central core and having a front extremity and a rear extremity; a first attachment line located at the front extremity of the external envelope; and a second attachment line located at the rear extremity of the external envelope; wherein the first attachment line and the second attachment line are for attachment of the absorbent product to the article of clothing; and wherein the absorbent product is free of means for adhesively attaching the garment-facing surface to the article of clothing.

According to various aspects, the present disclosure provides an article of clothing for absorption of urine leaks from a wearer, the article of clothing comprising: a crotch region having a front seam line and a rear seam line; an absorbent product having a first attachment line and a second attachment line; wherein the first attachment line coincides with the front seam line of the crotch region and the second attachment line coincides with the rear seam line of the crotch region; and wherein the absorbent product has a wearer-facing surface and a garment-facing surface opposite the wearer-facing and wherein the garment-facing surface is free of means for adhesively attaching the absorbent product to the crotch region of the article of clothing.

BRIEF DESCRIPTION OF THE DRAWINGS

A detailed description of embodiments of the present disclosure is provided below, by way of example only, with reference to the accompanying drawings, in which:

FIG. 1A: the absorbent product is in a substantially flat configuration (i.e., when not in use); FIG. 1B: the absorbent product is in a curved configuration (i.e., when in use);

FIGS. 5A, 5B and 5C show schematic representations of an external envelope of an absorbent product according to one embodiment of the present disclosure wherein FIG. 5A shows an external envelope having an attachment joint; FIG. 5B shows an external envelope having an attachment joint and one channel; and FIG. 5C shows an external envelope having one an attachment joint and two channels;

FIG. 8A: side view of the absorbent product and the undergarment; FIG. 8B: sketch view of a cross-section of FIG. 8A.

DETAILED DESCRIPTION

Figure 1A:
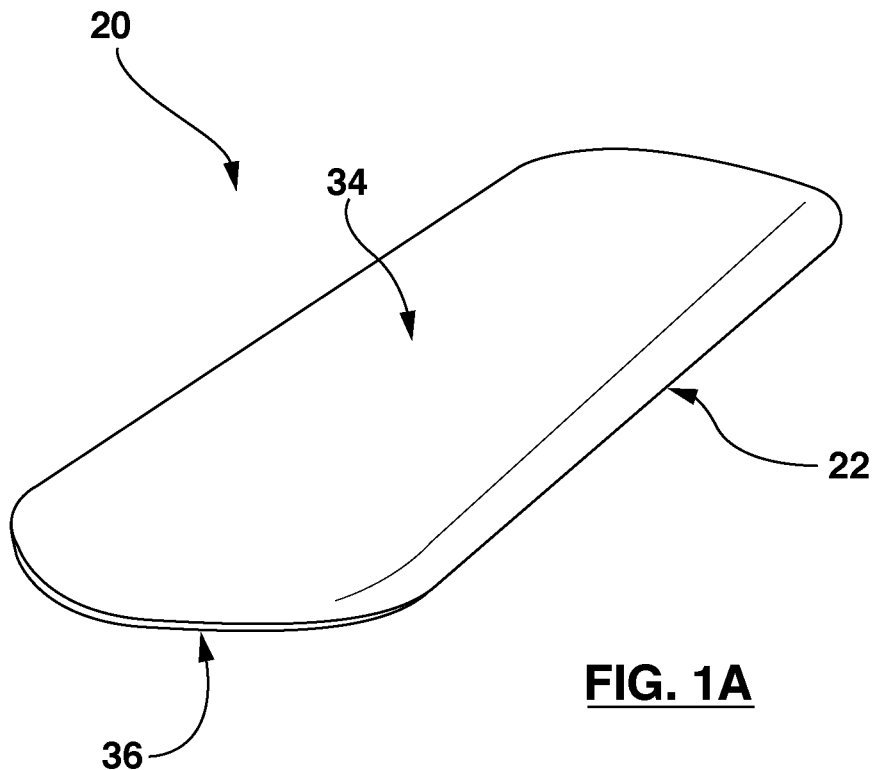
FIGS. 1A-1B show side elevation views of an absorbent product according to one embodiment of the present disclosure.

The present technology is explained in greater detail below. This description is not intended to be a detailed catalog of all the different ways in which the technology may be implemented, or all the features that may be added to the instant technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant technology. Hence, the following specification is intended to illustrate some particular embodiments of the technology, and not to exhaustively specify all permutations, combinations and variations thereof.

As used herein, the singular form "a," "an" and "the" include plural referents unless the context clearly dictates otherwise.

The term "about" is used herein explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

The expression "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

In one embodiment, the present disclosure relates to an absorbent product which is suitable for attachment to an article of clothing. In particular, the absorbent product of the present disclosure is suitable for attachment to the crotch portion of an article of clothing in order to absorb biological fluids expelled from the wearer of the article of clothing. In specific instances, the absorbent product of the present disclosure is used to absorb body fluids expelled from the wearer. In specific instances, the absorbent product of the present disclosure is used to absorb urinary leakage from the wearer. In some implementations of these embodiments, the wearer is a female wearer.

In one embodiment, the present disclosure relates to an article of clothing that comprises an absorbent product as defined herein. In some instances, the article of clothing is an undergarment, such as, but not limited to: underpants, underwear, pants, shorts, training pants, training shorts, leggings, or the like. In some implementations, the undergarment comprises a crotch region which may be defined by a front seam line (located at the front of the wearer when the undergarment is being worn) and a rear seam line (located at the rear of the wearer when the undergarment is being worn).

In some implementations of these embodiments, the absorbent product of the present disclosure as well as the articles of clothing comprising them, are washable and/or are reusable.

Figure 1B:
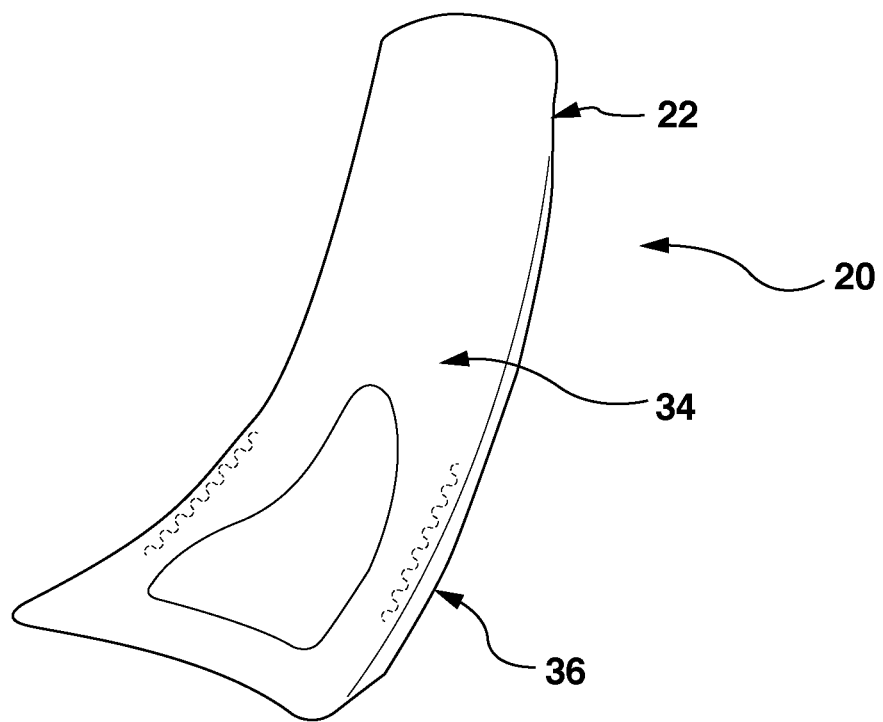

FIGS. 1A and 1B show an absorbent product 20 according to one embodiment of the present disclosure. The absorbent product 20 comprises a main body 22. The main body 22 has a wearer-facing surface 34 which corresponds to the surface of the absorbent product that is facing the skin of the wearer in a wear configuration and a garment-facing surface 36 opposite to the wearer-facing surface and facing the article of clothing in a wear configuration.

As used herein, the expression "wear configuration" refers to the position of the absorbent product when affixed to the crotch portion of an article of clothing.

Figure 2:
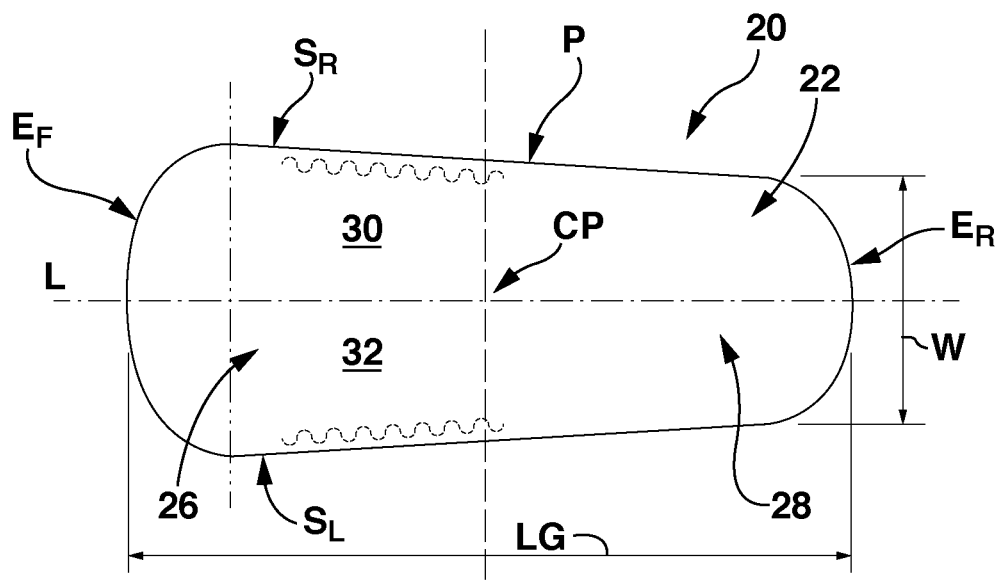
FIG. 2 shows a top view of the absorbent product according to one embodiment of the present disclosure.

As best seen in FIG. 2, the main body 22 of the absorbent product 20 has a longitudinal axis L bisecting the main body 22 into two longitudinal halves identified as 30 and 32 which are preferably identical in shape and size to ensure comfort of the user. The main body 22 also has a transversal axis T perpendicular to the longitudinal axis L intersecting the longitudinal axis L at a central point CP on the main body 22. The transvers axis T bisecting the main body 22 into a front portion 26 and a rear portion 28, the front portion 26 being located at the front of the article of clothing (not shown) in a wear configuration and the rear portion 28 being located at the back of the article of clothing (not shown) in a wear configuration. The main body 22 is defined by a periphery P comprising a front edge $E_F$, a rear edge $E_R$, a right lateral edge $S_R$ (located on the right side of the wearer in a wear configuration), and a left lateral edge $S_L$ (located on the left side of the wearer in a wear configuration).

In some implementations, the front portion 26 and the rear portion 28 have a substantially similar shape and size. In other implementations however, the front portion 26 and the rear portion 28 have a different shape and/or a different size. For example, the front portion 26 may be wider than the rear portion 28 (such as seen in FIG. 2), or the rear portion 26 may be wider than the rear portion 28. In further examples, the front portion 26 may be longer or shorter than the rear portion 28.

In some instances, the main body 22 has a length LG that is measured from the apex of the front edge $E_F$ to the apex of the rear edge $E_R$ and that is at least about 10 cm, at least about 12 cm, at least about 14 cm, at least about 16 cm, at least about 18 cm or at least about 20 cm.

In some instances, the main body 22 has a width W that is measured from the right lateral edge $S_R$ to the left lateral edge $S_R$ and that is at least about 2 cm, at least about 3 cm, at least about 4 cm, at least about 4.5 cm, at least about 5.0 cm, at least about 5.5 cm, at least about 6.0 cm, at least about 6.5 cm, at least about 7.0 cm, at least about 7.5 cm, at least about 8.0 cm, at least about 8.5 cm, at least about 9.0 cm, at least about 9.5 cm or at least about 10.0 cm. In some instances, such as illustrated in FIG. 2, the width W of the main body 22 varies along the length LG of the main body 22. In this embodiment, the width W of the main body 22 is greater at the front portion 26 than at the rear portion 28. It will be appreciated that, in this implementation, the width W of the main body increases from the rear portion 28 to the front portion 26. In some other instances, the width W of the main body 22 is greater at the rear portion 28 than at the front portion 26. It will be appreciated that, in these instances, the width W of the main body decreases from the rear portion 28 to the front portion 26.

Figure 3:
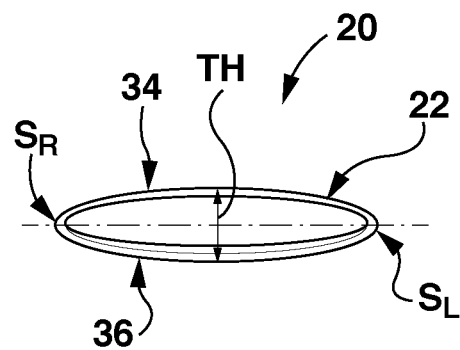
FIG. 3 shows a cross-sectional view of the absorbent product according to one embodiment of the present disclosure.

In some specific examples, and as best seen in FIG. 3, the main body 22 of the absorbent product 20 has a thickness TH that is measured from the wearer-facing surface 34 of the main body 22 to the garment-facing surface 36 of the main body 22 at the central point CP and that is at least about 0.5 cm, at least about 0.75 cm, at least about 1.0 cm, at least about 1.25 cm, or at least about 1.5 cm. In some implementations, the thickness TH of the main body 22 decreases towards the edges (i.e., $E_F$, $E_R$, $S_R$ and $S_L$) as seen in FIG. 3.

Figure 4:
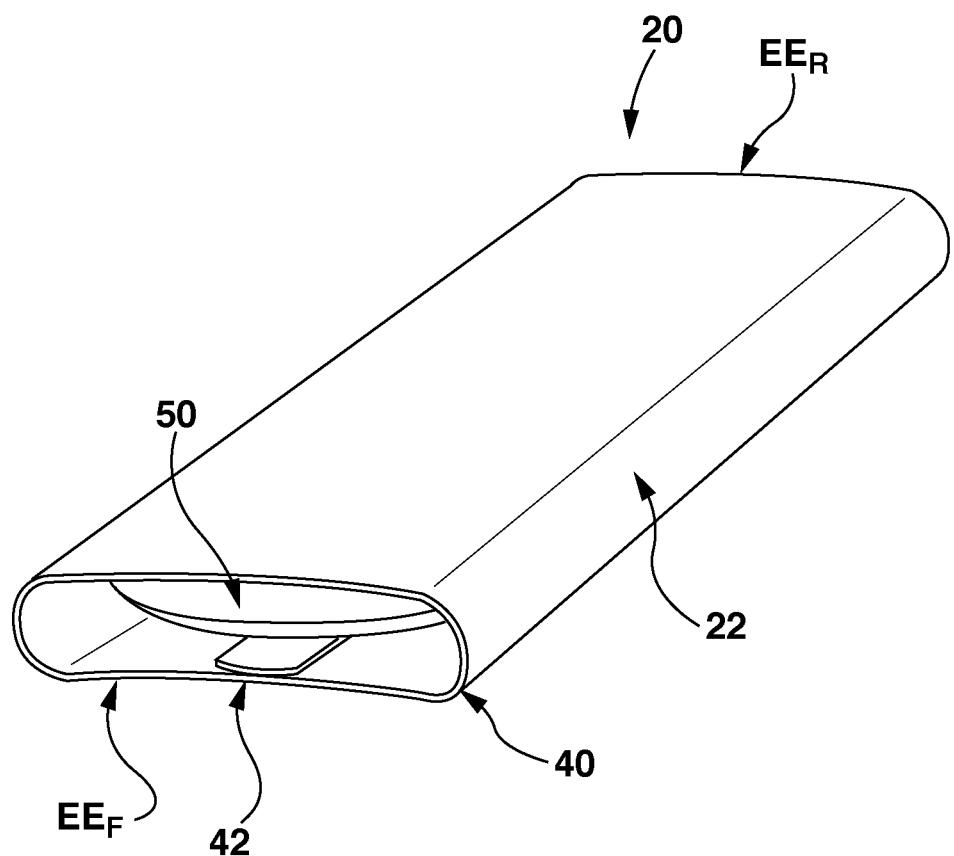
FIG. 4 shows a side elevation view of the absorbent product according to one embodiment of the present disclosure wherein the ends of the absorbent product are open (i.e., have not been closed)

In some embodiments, the main body 22 comprises an external envelope 40 and a central absorbent core 50. The external envelope 40 surrounds the central absorbent core 50 such as illustrated in FIG. 4. The external envelope 40 has a front extremity $EE_F$ and a rear extremity $EE_R$. The central absorbent core 50 has a front extremity $CE_F$ (not shown) and a rear extremity $CE_R$ (not shown). The front extremity $EE_F$ of the external envelope 40 and the front extremity $CE_F$ of the central absorbent core 50 coincide with the front edge $E_F$ of the front portion 26 of the main body 22, and the rear extremity $EE_R$ of the external envelope 40 and the rear extremity $CE_R$ of the central absorbent core 50 coincide with the rear edge $E_R$ of the rear portion 28 of the main body 22.

In some embodiments, the external envelope 40 is seamless. In such embodiments, the external envelope 40 acts as a sleeve around the central absorbent core 50 and the absorbent product 20 is assembled by inserting the central absorbent core 50 into the interior of the sleeve through either one of the front $EE_F$ and the rear $EE_R$ extremities of the external envelope 40. Once the central absorbent core 50 is inserted into the external envelope 40, the front $EE_F$ and/or the rear $EE_R$ extremities are closed. In some instances, the front $EE_F$ and/or the rear $EE_R$ extremities are sealed, stitched, sewed, or glued in order to close the two extremities of the sleeve to prevent the central absorbent core 50 from exiting the sleeve and to minimize movement of the central absorbent core 50 within the sleeve once the extremities are closed.

Figure 5A:
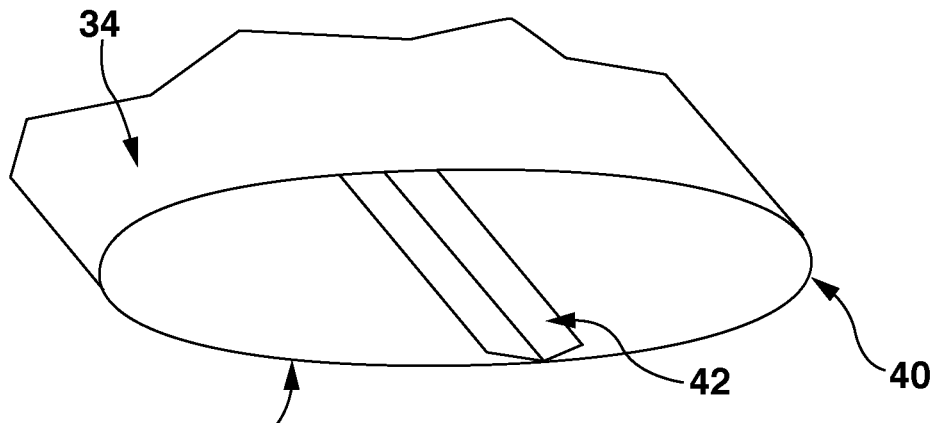

In some embodiments, the external envelope 40 is wrapped around the central absorbent core 50 and is closed or sealed on the garment-facing surface 36 along the longitudinal axis L. In this instance, the external envelope 40 comprises an attachment joint 42 (FIG. 4 and FIG. 5A) preferably located on the garment-facing surface 36 of the main body 22. The front $EE_F$ or the rear $EE_R$ extremities are then closed. In some instances, the front $EE_F$ or the rear $EE_R$ extremities are sealed, stitched, sewed, or glued in order to close the two extremities of the sleeve to prevent the central absorbent core 50 from exiting the sleeve and to minimize movement of the central absorbent core 50 within the sleeve once the extremities are closed. In some instances, attachment joint 42 may be accomplished by heat bonds, pressure bonds, ultrasonic bonds, dynamic mechanical bonds, or any other suitable attachment means or combinations of these attachment means as are known in the art.

Figure 5B:
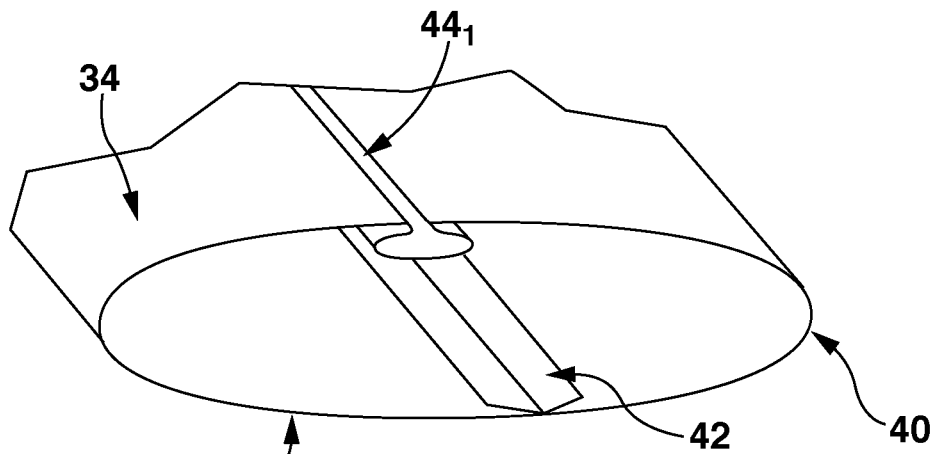
Figure 5C:
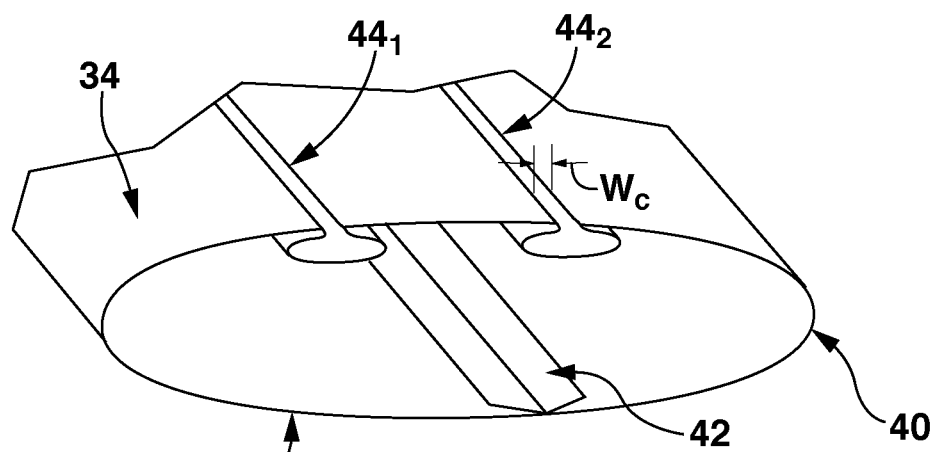

In some embodiments, such as shown in FIG. 5B and FIG. 5C, the wearer-facing surface 34 of the external envelope 40 comprises at least one channel 44 which is at least partially oriented in the longitudinal direction of the main body 22 (i.e., has a longitudinal vector component). Other channels may be at least partially oriented in the lateral direction (i.e., has a lateral vector component) or in any other direction. As used herein, the plural form "channels" means "at least one channel". The channels may have a length (not shown) projected on the longitudinal axis L of the main body 22 article that is at least 10% of the length LG of the main body 22. The channels may be continuous but it is also envisioned that the channels may be intermittent. The external envelope 40 may also comprise more than one channel, for example, at least two (see elements $44_1$ and $44_2$ on FIG. 5C), at least 3, at least 4, at least 5, or at least 6 or more channels. When present as symmetrical pairs relative to the longitudinal axis L, the channels may be spaced apart from one another over their whole longitudinal dimension. The smallest spacing distance between the channels may be for example: at least 5 mm, at least 10 mm, or at least 15 mm.

To reduce the risk of fluid leakages, the channels may not extend up to any of the edges of the absorbent product 20. In some instances, the smallest distance between the end of a channel and the extremity of both the front edge EF and the rear edge $E_R$ is at least 5 mm, at least 7 mm, or at least 10 mm. The channels may have a width $W_C$ along at least part of its length which is at least 1 mm, at least 2 mm, at least 3 mm, at least 4 mm, up to for example 20 mm, 16 mm, or 12 mm, for example. The width of the channel may be constant through substantially the whole length of the channel or may vary along its length.

In some instances, the channels accept biological fluids from the wearer and distribute the biological fluids to the central absorbent core 50 and accelerate absorption by the central absorbent core 50. In some instances, the channels improve flexibility of the absorbent product 20.

In some instances, the channels are created by folds, bends or wrinkles created in the external envelope 40 according to techniques and methods well-known in the art.

Figure 6:
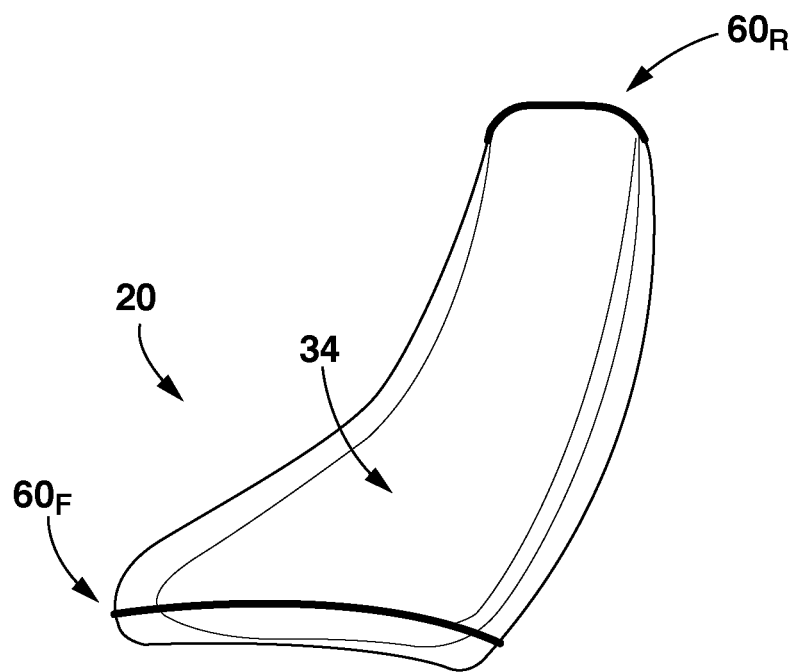
FIG. 6 shows a top view of an absorbent product according to one embodiment of the present disclosure wherein the absorbent product is in a wear or use configuration.
Figure 7:
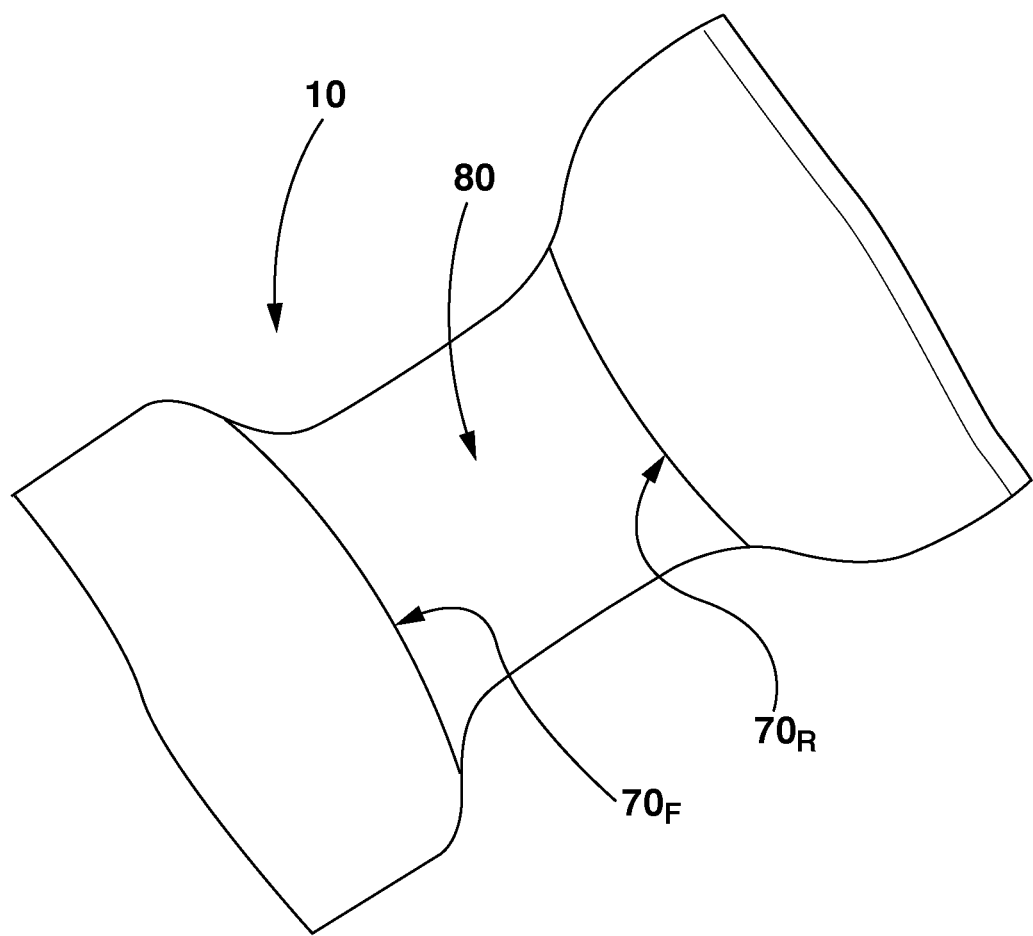
FIG. 7 shows a schematic representation of a top partial view of an enlarged crotch region of an undergarment.

FIG. 6 shows an embodiment of the absorbent product 20 of the present disclosure wherein the main body 22 comprises attachment lines $60_F$ and $60_R$ respectively located at the front $EE_F$ and at the rear $EE_R$ extremities of the external envelope 40. Attachment lines $60_1$ and $60_2$ attach the absorbent product 20 to the crotch region 80 of the article of clothing 10. Preferably, attachment lines $60_1$ and $60_2$ coincide with the front seam line $70_F$ and the rear seam line $70_R$ of the crotch portion respectively, wherein the front seam line $70_F$ and the rear seam line $70_R$ respectively delimit the front portion and the rear portion of the crotch region 80, as illustrated in FIG. 7. In some implementations, attachment line $60_F$ and front seam line $70_F$ are interweaved forming one attachment line at the front of the main body 22 and attachment lines $60_R$ and front seam line $70_R$ are also interweaved forming one attachment line at the rear of the main body 22. In this implementation, the attachment lines $60_1$ and $60_2$ are the only points of attachment of the absorbent product 20 to the article of clothing 10.

Contrary to some absorbent products currently commercially available for urinary leakage, the right lateral edge $S_F$ and the left lateral edge $S_R$ of the main body 22 of the absorbent product are not attached to the article of clothing resulting in the garment-facing surface 36 of the main body 22 not having any points of attachment to the crotch region of the article of clothing 10. Such configuration allows to minimize the number of perforations in the absorbent product 20 (created by, for example, the stiches). In addition, having only the two attachment lines $60_1$ and $60_2$ one at the front extremity and another one at the rear extremity of the absorbent product 20 allows the absorbent product 20 to move partially independently from the crotch portion 80 of the article of clothing 10 while remaining attached to the article of clothing 10 at the front and the rear extremities.

In some embodiments, the absorbent product of the present disclosure is non-adhesively connected to the article of clothing. As used herein, the expression "non-adhesively connected" means that the garment-facing 36 surface of the absorbent product 20 is not retained on the article of clothing by any adhesive means as seen in conventional sanitary napkins or other similar products. As such, in some embodiments, the garment-facing surface 36 of the main body 22 does not comprise means for adhesively connecting the absorbent product 20 to the article of clothing 10.

Figure 8A:
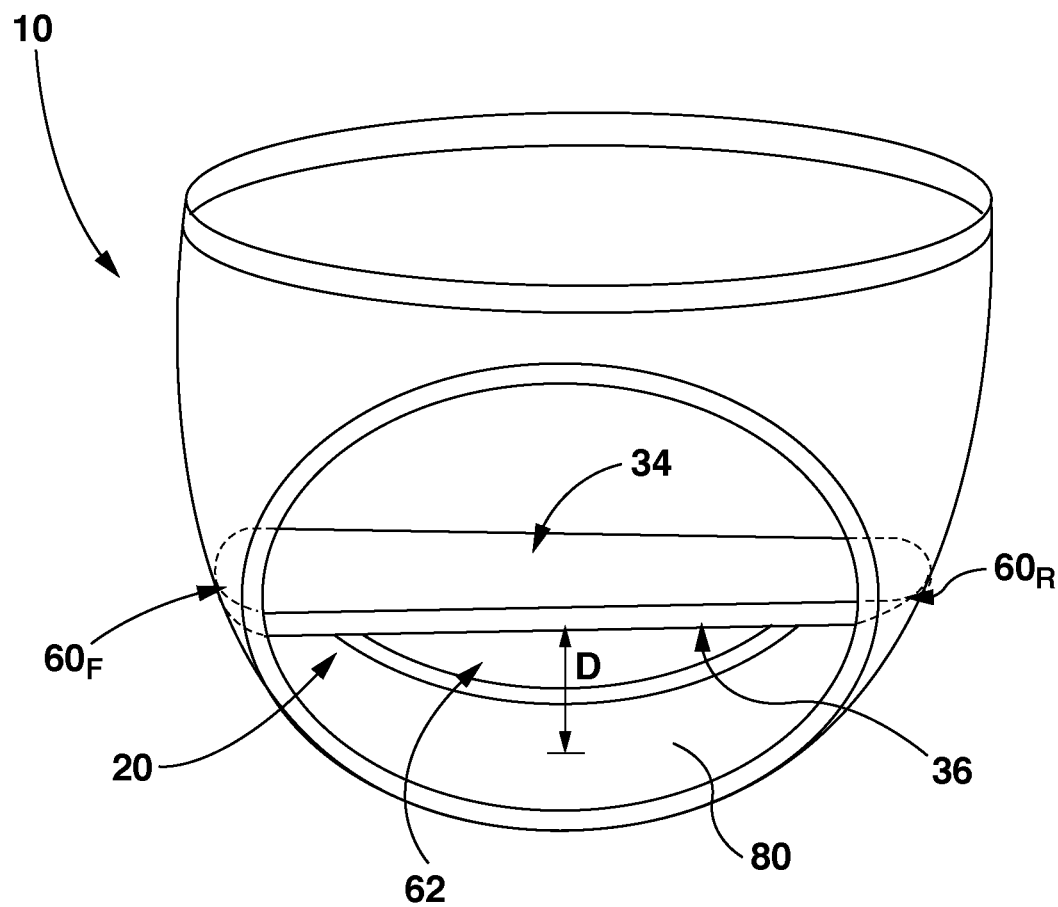
FIGS. 8A-8B show schematic representations of a side view of an undergarment having an absorbent product according to one embodiment of the present disclosure non-adhesively connected to the crotch region of the undergarment.

FIG. 8A illustrates an embodiment of the present disclosure wherein the absorbent product 20 is displaced from the crotch region 80 of an article of clothing 10 while remaining attached to the article of clothing 10 at the attachment lines $60_F$ and $60_R$ creating displacement zone 62—it will be understood that such embodiment is achieved when the article of clothing 10 is not being worn by a user and when the absorbent product 20 is being held in a flat configuration while the article of clothing is allowed to hang loose from the attachment lines $60_F$ and $60_R$. Displacement zone 62 (also shown in FIG. 8B) represents the area located immediately above the crotch region 80 of the article of clothing 10 in which the absorbent product 20 is movable. In some implementations, displacement zone 62 provides freedom of movement for the absorbent product 20 to adjust to movement of the wearer. In addition, displacement zone 62 minimises the points of contact and/or attachment between the absorbent product 20 and the article of clothing 10, thereby decreasing the risk of fluid leakage.

Figure 8B:
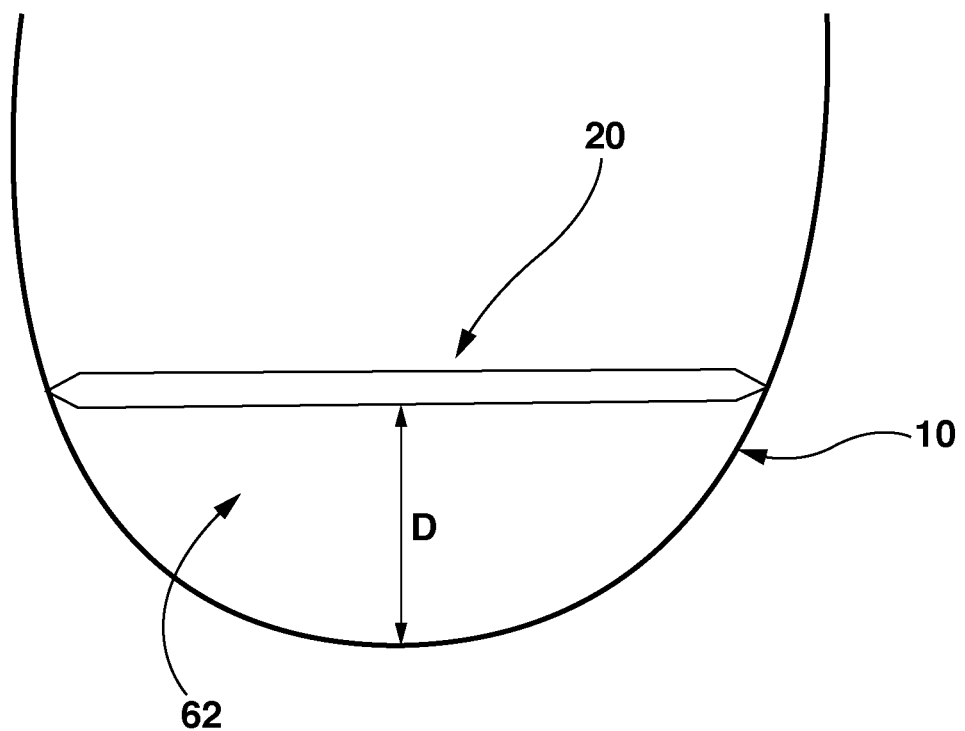

In some implementations, displacement zone 62 has a displacement distance D (FIG. 8B) which is measured from the central point CP (not shown) on the garment-facing surface 36 of the main body 22 when the main body 22 is in a substantially flat (i.e., non-curved) configuration, to the lowest point on the wearer-facing surface of the crotch region (surface of the crotch region that is in contact with the skin of the wearer when worn) when the article of clothing 10 is allowed to hang from the flat absorbent product 20 while being attached at the attachment lines $60_F$ and $60_R$ (FIG. 8B). In a substantially flat configuration, there is substantially no curvature along the longitudinal axis L and substantially no curvature along the transversal axis T of the main body 22. The central point is defined by the intersection of the longitudinal axis L and the transversal axis T on the garment-facing surface 36 of the main body 22. In some instances, D is at least about 0.5 cm, at least about 1 cm, at least about 1.5 cm, at least about 2 cm, at least about 2.5 cm, at least about 3 cm, at least about 3.5 cm, at least about 4 cm, at least about 4.5 cm, at least about 5 cm, at least about 5.5 cm, at least about 6 cm, at least about 6.5 cm, at least about 7 cm, at least about 7.5 cm, at least about 8 cm, at least about 8.5 cm, at least about 9 cm, at least about 9.5 cm, at least about 10 cm, or is between about 0.5 cm and about 10 cm; or is between about 1 cm and 10 cm, or is between about 1 cm and about 5 cm. In some instances, the displacement zone 62 has a semicircle or a semiovale (half-ovale) shape.

In some embodiments, the external envelope 40 is made of permeable materials allowing transfer of mixtures or other of biological fluids to the central absorbent core 50. For example, the external envelope 40 may be a relatively low density, bulky, high-loft non-woven web material. The external envelope 40 may be composed of only one type of fiber, such as polyester or polypropylene or it may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. In some implementations, the external envelope 40 includes polyethylene or polypropylene or a combination of both. In a specific example, the external envelope 40 is a through-air bonded bicomponent of polyethylene/polypropylene sheet/core non-woven. Bi-component fibers may be made up of a polyester core and a polyethylene sheath. The use of appropriate bi-component materials may result in a fusible non-woven fabric and may also improve softness.

The external envelope 40 preferably has a relatively high degree of wettability, although the individual fibers comprising the cover may not be particularly hydrophilic. In some implementations, the external envelope 40 may comprise relatively large pores. This is because the external envelope 40 is intended to take-up body fluid rapidly and to transport it away from the body and the point of deposition. Advantageously, the fibers which make up the external envelope 40 should not lose their physical properties when they are wetted, in other words they should not disintegrate, collapse or lose their resiliency when subjected to water or body fluid. The external envelope 40 may be treated to allow fluid to pass through it readily. The external envelope 40 also functions to transfer the fluid quickly to the central absorbent core 50.

In a specific implementation, the external envelope 40 is hydrophobic and perforated.

When composed of synthetic hydrophobic fibers, the external envelope 40 may be treated with a surfactant to impart the desired degree of wettability.

The external envelope 40 may also be made of polymer film having large pores. Because of such high porosity, the film accomplishes the function of quickly transferring body fluid to the inner layers of the absorbent system.

In a specific example, the external envelope 40 is perforated to create channels so as to keep the skin of the wearer dry. The external envelope 40 may be embossed to the absorbent system 44 in order to aid in promoting fluid transport by fusing the cover to the next layer. Such fusion may be effected locally, at a plurality of sites or over the entire contact surface of external envelope 40.

The central absorbent core 50 is surrounded by the external envelope 40 as best seen in FIG. 4. In some instances, the central absorbent core 50 provides the means of receiving body fluid from the external envelope 40 and for holding it.

In some embodiments, the external envelope 40 may have a wearer-facing surface that is liquid permeable and a garment-facing surface that is liquid impermeable. In such embodiments, the external envelope 40 is made from a combination of different materials. The impermeable material is positioned towards the bottom side of the absorbent core and prevents the exudates absorbed and contained therein from soiling the article of clothing. The impermeable material may for example be or comprise a thin plastic film such as a thermoplastic film having a thickness of about 0.01 mm to about 0.05 mm. Exemplary films include those manufactured by Tredegar Corporation, based in Richmond, Va., and sold under the trade name CPC2 film. Other suitable impermeable materials may include breathable materials which permit vapors to escape from the article of clothing while still preventing exudates from passing through the impermeable material. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097.

The permeable material and the impermeable material of the external envelope 40 may be joined by any attachment means known in the art. Suitable attachment means may include a uniform continuous layer of adhesive, a patterned layer of adhesive, or an array of separate lines, spirals, or spots of adhesive. Other suitable attachment means include several lines of adhesive filaments which are swirled into a spiral pattern. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

In some embodiments, the central absorbent core 50 is, preferably, denser than and has a larger proportion of smaller pores than the external envelope 40. These attributes allow the central absorbent core 50 to contain body fluid and hold it away from the outer side of the external envelope 40, thereby preventing the fluid from re-wetting the external envelope 40 and its surface.

In some embodiments, the absorbent core 50 is made of absorbent materials. By "absorbent material" it is meant a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 50%, for example at least 75%, or at least 80%, or at least 85%, or at least 90%, or at least 95% and even up to and including 100% of the weight of the absorbent material contained within the absorbent core. The absorbent material may in particular comprises less than 10% weight percent of natural or synthetic fibers, or less than 5% weight percent, or even be substantially free of natural and/or synthetic fibers. The absorbent material may advantageously comprise little or no airfelt (cellulose) fibers, in particular the absorbent core may comprise less than 15%, 10%, 5% airfelt (cellulose) fibers by weight of the absorbent core, or even be substantially free of cellulose fibers.

The absorbent core 50 may further comprise adhesive for example to help immobilizing the SAP and/or to ensure integrity of the absorbent core, in particular when the absorbent core is made of two or more substrates.

The absorbent material may be a continuous layer present within the absorbent core. In other embodiments, the absorbent material may be comprised of individual pockets or stripes of absorbent material enclosed within the absorbent core. In the first case, the absorbent material may be for example obtained by the application of a single continuous layer of absorbent material. The continuous layer of absorbent material, in particular of SAP, may also be obtained by combining two absorbent layers having discontinuous absorbent material application pattern wherein the resulting layer is substantially continuously distributed across the absorbent particulate polymer material area.

In other embodiments, the central absorbent core 50 is made of a foam material. In some implementations of these embodiments, the foam material is an open-cell foam material. As used herein, the expression "open-cell foam" refers to a foam material wherein the gas pockets connect with each other.

The central absorbent core 50 can be prepared over a wide range of basis weights. The central absorbent core 50 may have a basis weight in the range of from about 1000 g/m$^2$ to about 1500 g/m$^2$. In a specific example, the basis weight ranges from about 1250 g/m$^2$ to about 1400 g/m$^2$. In another specific example, the basis weight ranges from about 1250 g/m$^2$ to about 1350 g/m$^2$ and, more specifically, ranges from about 1295 g/m$^2$ to about 1335 g/m$^2$.

The central absorbent core 50 has a thickness which can be of up to about 2.0 cm. For example, of up to about 0.5 cm, up to about 0.75 cm, up to about 1.0 cm, up to about 1.25 cm, up to about 1.5 cm, or up to about 2.0 cm. The person of skill can readily prepare an absorbent core 46 having a suitable thickness without undue experimentation.

In some embodiments, the central absorbent core 50 may comprise superabsorbent polymers. Superabsorbent polymers are well known in the art. For the purposes of the present disclosure, the term "superabsorbent polymer" (or "SAP") refers to materials which are capable of absorbing and retaining at least about 10 times their weight in body fluids under a 0.5 psi pressure. The superabsorbent polymer particles which can be suitable for use in the present disclosure may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles which can be suitable for use in the present disclosure are crosslinked polyacrylates, such as the product offered by Sumitomo Seika Chemicals Co., Ltd. Of Osaka, Japan, under the designation of SA60N Type II, and the product offered by Chemdal International, Inc. of Palatine, Ill., under the designation of 2100A.

In some embodiments, the attachment lines $60_F$ and $60_R$ are made by a coverstitch machine or by a sewing machine.

EXAMPLE 1—DIMENSIONS OF ABSORBENT ARTICLES

Table 1 below presents examples of sizes of the main body of an absorbent article according to one embodiment of the present disclosure for the specified sizes of article of clothing.

TABLE 1

Dimensions of the main body

| Size of undergarment | Length | Width | Thickness |
|---|---|---|---|
| Extra small (XS) | Central absorbent core: 15.4 cm<br>External envelop: 17.3 cm | 5 cm | 1 cm |
| Small (S) | Central absorbent core: 16.7 cm<br>External envelop: 18.5 cm | 5 cm | 1 cm |
| Medium (M) | Central absorbent core: 18 cm<br>External envelop: 20 cm | 5 cm | 1 cm |
| Large (L) | Central absorbent core: 19.3 cm<br>External envelop: 21.1 cm | 5 cm | 1 cm |
| Extra large (XL) | Central absorbent core: 21.2 cm<br>External envelop: 23.1 cm | 5 cm | 1 cm |

The central absorbent core was made of 4 layers of materials:
- a first layer made of 75% Polyester, 25% Polyurethane (155 grams per square meter (GSM));
- a second layer having a wearer-facing portion made of 70% bamboo viscose, 30% organic cotton, and a garment-facing portion made of 100% wicking polyester (430 à 470 GSM);
- a third layer made of 2 plies of a blend of cellulosic fibers from cotton/tencel/bamboo/other interspersed with polyester nylon (235 GSM); and
- a fourth layer made of 100% polyester (240 GSM).

The first layer is at the wearer-facing surface of the central absorbent core and the fourth layer is at the garment-facing surface of the central absorbent core, the second layer is placed beneath the first layer and on top of the third layer and the third layer is beneath the second layer and on top of the fourth layer.

Any feature of any embodiment discussed herein may be combined with any feature of any other embodiment discussed herein in some examples of implementation.

Certain additional elements that may be needed for operation of certain embodiments have not been described or illustrated as they are assumed to be within the purview of those skilled in the art. Moreover, certain embodiments may be free of, may lack and/or may function without any element that is not specifically disclosed herein.

Although various embodiments and examples have been presented, this was for the purpose of describing, but not limiting, the invention. Various modifications and enhancements will become apparent to those skilled in the art and are within the scope of the invention, which is defined by the appended claims.

All documents referred to herein are incorporated by reference.

The invention claimed is:

1. An absorbent product for attachment to an article of clothing, the absorbent product comprising a wearer-facing surface and a garment-facing surface opposite the wearer-facing surface, the absorbent product comprising a main body, wherein the main body comprises:
   a) a central absorbent core;
   b) an external envelope placed around the central core and having a front extremity and a rear extremity, and a channel extending between the front extremity and the rear extremity without reaching the front extremity and the rear extremity;
   c) a first attachment line located at the front extremity of the external envelope; and
   d) a second attachment line located at the rear extremity of the external envelope;

wherein the first attachment line and the second attachment line are for attachment of the absorbent product to the article of clothing; and wherein the absorbent product is free of means for adhesively attaching the garment-facing surface to the article of clothing; and wherein the external envelope has an external face, and wherein the channel extends inwardly from a first width to a second width greater than and inward from the first width.

2. The absorbent product as defined in claim 1, wherein the first attachment line and the second attachment line are seam lines.

3. The absorbent product as defined in claim 1, wherein the article of clothing has a crotch portion defined at least by a front seam line and a rear seam line.

4. The absorbent product as defined in claim 3, wherein the first attachment line coincides with the front seam line of the crotch portion.

5. The absorbent product as defined in claim 3, wherein the second attachment line coincides with the rear seam line of the crotch portion.

6. The absorbent product as defined in claim 4, wherein the first attachment line is interweaved with the front seam line of the crotch portion.

7. The absorbent product as defined in claim 4, wherein the second attachment line is interweaved with the rear seam line of the crotch portion.

8. The absorbent product as defined in claim 1, wherein the article of clothing is selected from undergarment, underwear, underpants, pants, leggings, tights, and shorts.

9. The absorbent product as defined in claim 1, wherein the absorbent product is for absorption of urine leaks.

10. The absorbent product as defined in claim 1, wherein the channel is seamless.

11. An article of clothing for absorption of urine leaks from a wearer, the article of clothing comprising:
   a crotch region having a front seam line and a rear seam line;
   an absorbent product having a first attachment line and a second attachment line, the absorbent product comprising a main body comprising:
      a central absorbent core; and
      an external envelope placed around the central core and having a front extremity and a rear extremity, and a channel extending between the front extremity and the rear extremity without reaching the front extremity and the rear extremity;
   wherein the first attachment line coincides with the front seam line of the crotch region and the second attachment line coincides with the rear seam line of the crotch region; and
   wherein the absorbent product has a wearer-facing surface and a garment-facing surface opposite the wearer-facing and wherein the garment-facing surface is free of means for adhesively attaching the absorbent product to the crotch region of the article of clothing; and
   wherein the external envelope has an external face, and wherein the channel extends inwardly from a first width to a second width greater than and inward from the first width.

12. The article of clothing as defined in claim 11, wherein the absorbent product comprises a main body, wherein the main body comprises:
   a) a central absorbent core;
   b) an external envelope placed around the central core and having a front extremity and a rear extremity;

wherein the first attachment line is located at the front extremity of the external envelope and the second attachment line is located at the rear extremity of the external envelope.

13. The article of clothing as defined in claim 11, wherein the garment-facing surface of the absorbent product and the crotch region define a displacement zone in which the absorbent product is movable.

14. The article of clothing as defined in claim 13, wherein the displacement zone has a displacement distance.

15. The article of clothing as defined in claim 11, wherein the first attachment line and the second attachment line are seam lines.

16. The article of clothing as defined in claim 11, wherein the channel is seamless.

17. An absorbent product for attachment to an article of clothing, the absorbent product comprising a wearer-facing surface and a garment-facing surface opposite the wearer-facing surface, the absorbent product comprising a main body, wherein the main body comprises:
   a) a central absorbent core, comprising at least four layers of absorbent materials, including:
      a first layer of absorbent materials including one or more of polyester and polyurethane;
      a second layer of absorbent materials including one or more of bamboo viscose, cotton, and polyester;
      a third layer of absorbent materials including one or more of cellulose and nylon; and
      a fourth layer of absorbent materials including polyester;
   b) an external envelope placed around the central core and having a front extremity and a rear extremity;
   c) a first attachment line located at the front extremity of the external envelope; and
   d) a second attachment line located at the rear extremity of the external envelope;
   wherein the first attachment line and the second attachment line are for attachment of the absorbent product to the article of clothing; and
   wherein the absorbent product is free of means for adhesively attaching the garment-facing surface to the article of clothing.

18. The absorbent product as defined in claim 17, wherein the first attachment line and the second attachment line are seam lines.

19. The absorbent product as defined in claim 17, wherein the article of clothing has a crotch portion defined at least by a front seam line and a rear seam line.

20. An article of clothing for absorption of urine leaks from a wearer, the article of clothing comprising:
   a crotch region having a front seam line and a rear seam line;
   an absorbent product having a first attachment line and a second attachment line, the absorbent product comprising a main body comprising:
      a central absorbent core; and
      an external envelope placed around the central core and having a front extremity and a rear extremity, and a channel extending between the front extremity and the rear extremity without reaching the front extremity and the rear extremity;
   wherein the first attachment line coincides with the front seam line of the crotch region and the second attachment line coincides with the rear seam line of the crotch region; and
   wherein the absorbent product has a wearer-facing surface and a garment-facing surface opposite the wearer-facing and wherein the garment-facing surface is free of means for adhesively attaching the absorbent product to the crotch region of the article of clothing, wherein the central absorbent core comprises at least four layers of absorbent materials, including:
a first layer of absorbent materials including one or more of polyester and polyurethane;
a second layer of absorbent materials including one or more of bamboo viscose, cotton, and polyester;
a third layer of absorbent materials including one or more of cellulose and nylon; and
a fourth layer of absorbent materials including polyester.

\* \* \* \* \*